United States Patent [19]

Hale

[11] Patent Number: 5,336,157
[45] Date of Patent: Aug. 9, 1994

[54] PENILE CLAMP FOR IMPOTENCE

[76] Inventor: Ralph Hale, 37 Linksland Dr., Hutchinson, Kans. 67502

[21] Appl. No.: 986,440

[22] Filed: Dec. 4, 1992

[51] Int. Cl.⁵ .............................................. A61B 17/00
[52] U.S. Cl. ...................................... 600/41; 606/158; 606/151; 128/843; 24/300; 24/543
[58] Field of Search ........................ 606/151, 157–158; 600/41; 128/842–843; 24/300, 129 D, 543

[56] References Cited

U.S. PATENT DOCUMENTS

| | | | |
|---|---|---|---|
| 2,581,114 | 1/1952 | Larson | 600/41 |
| 3,511,230 | 5/1970 | Strong | 600/41 |
| 3,612,047 | 10/1971 | Nesbit | 600/41 |
| 3,636,948 | 1/1992 | Atchley | 600/41 |
| 3,794,020 | 2/1974 | Bagby | 600/41 |
| 4,203,432 | 5/1980 | Koch | 600/41 |
| 4,240,413 | 12/1980 | Hanus | 600/41 |
| 5,002,552 | 3/1991 | Casey | 606/157 |

*Primary Examiner*—Stephen C. Pellegrino
*Assistant Examiner*—Gary Jackson

[57] ABSTRACT

This invention is a therapeutic clamp intended to help males with impotence, or what should be more properly called, erectile dysfunction. The clamp consists of two hinged rods having elastic bands causing the rods to exert pressure on the sides of the penis, thereby restricting flow of blood from the penis in order to maintain an erection without interfering with flow of blood into the penis, or obstructing the urethra.

2 Claims, 1 Drawing Sheet

PENILE CLAMP FOR IMPOTENCE

BACKGROUND OF THE INVENTION

Impotence in men results from a variety, and at times a mixture, of physiological and psychological conditions with a common feature being inability to maintain erection of the penis for a sufficient length of time to complete sexual intercourse. Normally, sexual arousal in healthy males results in the retention of blood in venous sinuses which extend along the length of the sides of the penis (corpus cavernosa, FIG. 1), which causes the penis to become stiff and erect. Numerous non-surgical devices and techniques have been proposed to manage this problem.

Some men with impotence are able to achieve an erection, but are unable to maintain it. In others, it is necessary to draw blood into the penis with an apparatus producing vacuum suction (described by: Witherington, R., J. Urol., 141:320, 1989), but in either case, the use of a constrictive device is needed to keep the venous sinuses filled.

U.S. Pat. Nos. 2,581,114, 2,818,855, 3,511,230, 3,612,047, 3,636,948, 3,759,253, 3,794,020, and 4,203,432 are examples of these constrictive devices. All of these are designed to put pressure on the penis in various ways in order to retard the flow of blood from the venous sinuses, and all but three of these inventions encircle the penis, which presents special problems. One of the most commonly used encircling devices is described in U.S. Pat. No. 3,759,253, and it is effective in maintaining an erection. However, it requires a lubricant in order to put it on. Also, once this device is in place on an erect penis, it is neither easy to remove, replace, or reposition, because of the looseness of the skin of the shaft of the penis.

There is a distinct advantage in using a device which does not completely encircle the penis. The three cited patents which are not encircling, also have disadvantages. U.S. Pat. No. 3,794,020 is difficult to manufacture, as the mechanism for producing pressure is a ratchet. Also, it is designed to put pressure on the dorsal veins FIG. 1), whereas, lateral pressure at the base of the penis is the more desired action. U.S. Pat. No. 3,511,230 presents difficulty for the user, since it requires considerable education and aptitude to operate successfully, because the method of producing pressure is by the action of the user's legs. U.S. Pat. No. 3,612,046 is, also, of complex construction, being made of an inner core of rigid material with an outer coating of spongy material. Like the invention about to be described, it consists of two legs, hinged at one end and open at the opposite end, but unlike my invention, it is used with the open end extending above the penis, with an elastic band attached to one leg at the open end. When used, the elastic band is looped around the two legs, in order to put pressure on the sides of the penis.

SUMMARY OF THE INVENTION

My invention is a clamp, designed to assist males who have difficulty in maintaining an erection, which clamp does not encircle the penis, but puts pressure only on the sides of the penis in order to retard the flow of venous blood, which pressure is adjustable, and which clamp is easy to put in place, remove, replace, and reposition while being worn. The clamp does not occlude the urethra or prevent arterial blood from entering the penis.

DETAILED DESCRIPTION OF THE INVENTION

Figure 1:
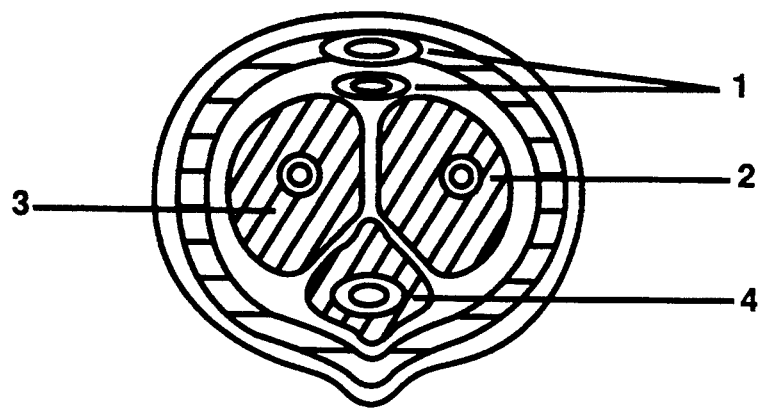
FIG. 1 shows a cross section of the penis, identifying structures of importance to this invention.
Figures 2, 3:
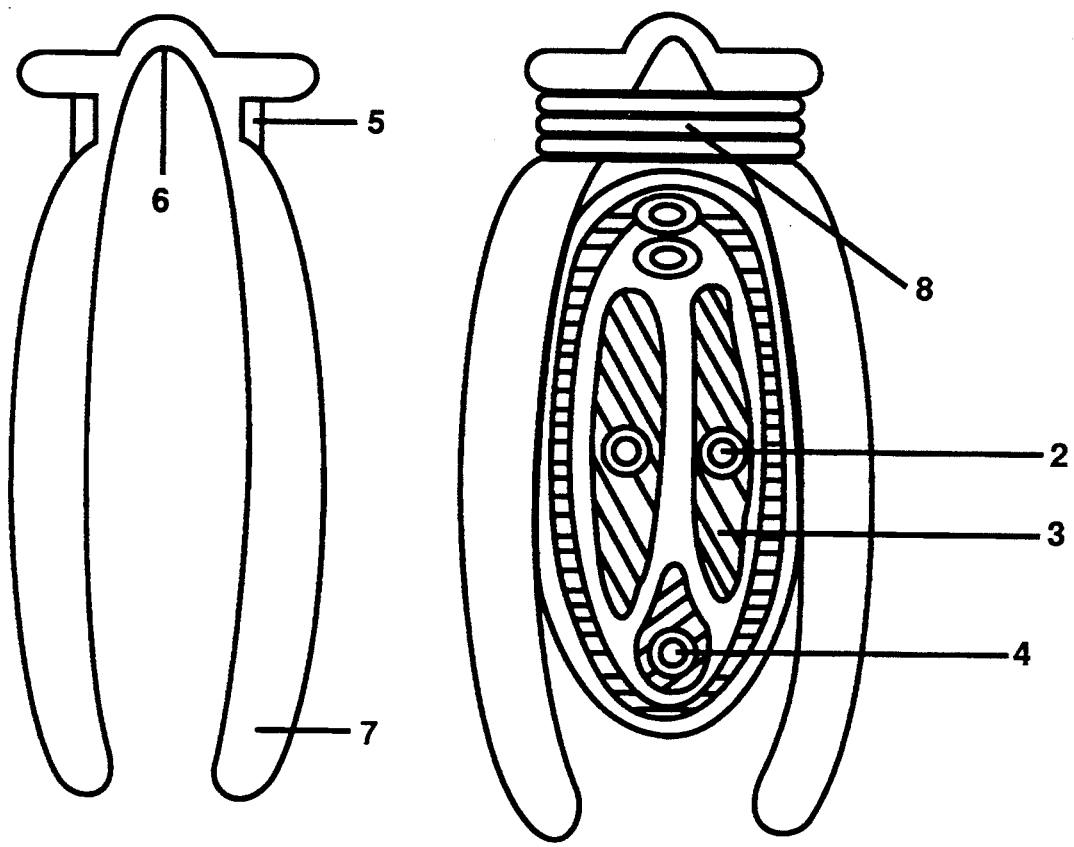
FIG. 2 is a drawing of the clamp, which consists of two rods (1), connected at one end by a flexible hinge (2), and open at the opposite end. Notches (3), near the hinged end, are to hold elastic bands.
FIG. 3 shows a cross section of the penis with the clamp in place.

This invention is a clamp, simple to manufacture, which may be made of any material, but which is preferably molded of one piece of plastic with suitable properties, which are: reasonably rigid in thick dimensions, but flexible enough to be hinge, if thin; and durable, if used as a hinge. It consists of two rods (1), which preferably are of sufficient length to extend a little beyond the diameter of the penis. The rods may be any shape, but ideally they should be slightly curved, with the concave sides opposing each other, as shown in FIG. 2. The rods are connected at one end by a hinge (2), and open at the other end so they can be spread apart. Again, the hinge may be any shape, but functions better if curved as shown in FIG. 2. The curve of the hinge may extend either below or above the end of the rods, but the preferred configuration is as illustrated. Elastic bands are placed around the rods in notches (3) in order to produce the desired inward pressure. This pressure may be changed to suit individual needs by increasing or decreasing the tension of the elastic bands. Pressure must be firm in order to retain blood in the venous sinuses, but not so strong as to cause discomfort.

To use, the rods are spread apart, and the clamp is placed at the base of the erect penis as close as possible to the abdominal wall, so that the rods will exert pressure on the sides of the penis at the base, when released. When in place, the hinged end is above and the open end is below the penis, FIG. 3. If necessary, the position of the clamp may easily be adjusted while being worn, by again spreading the rods, and moving the clamp to the desired position. The clamp will retain blood in the penis by inhibiting venous return from the cavernous sinuses but will not greatly interfere with the flow of blood through the central arteries since they are protected by the turgid corpora cavernosae; nor does the clamp occlude the urethra, FIG. 3.

What is claimed is:

1. A therapeutic clamp for assisting in maintenance of erection in the male penis, comprising a single piece of molded plastic, consisting of a pair of rods having distal and proximal ends and being of generally "C" shape configuration, wherein said pair of rods is connected at said proximal ends by a mid-portion; said mid-portion having a reduced thickness across a transverse region thereof, forming a flexible hinge permitting said rods to be spread apart, said rods having clamping surfaces curved toward each other; said rods further having notches on an outer surface opposite said clamping surfaces adjacent to the hinge, said notches to receive elastic bands transversely of said rods wherein the clamp pressure can be adjusted by manipulation of said bands.

2. The therapeutic clamp, defined in claim 1, further comprises elastic bands adapted to supply pressure on the sides of the penis, whereby the pressure may be adjusted to meet individual needs by changing the tension of the bands.

* * * * *

UNITED STATES PATENT AND TRADEMARK OFFICE
CERTIFICATE OF CORRECTION

PATENT NO. : 5,336,157
DATED : August 9, 1994
INVENTOR(S) : Hale

It is certified that error appears in the above-indentified patent and that said Letters Patent is hereby corrected as shown below:

Col. 2, line 4, after "invention" insert --These are: deep and superficial dorsal veins (1), central arteries (2), corpora cavernosa, (3), and urethra (4).

Col. 2, line 7, change "(2)" to --(6)--. and change "(3)" to --(5)--.
Col. 2, line 8, after bands add --(8)--

Col. 2, line 23, change "(2)" to --(6)--.

Col. 2, line 29, change "(3)" to --(5)--.

Signed and Sealed this

Eleventh Day of April, 1995

Attest:

BRUCE LEHMAN

*Attesting Officer*     *Commissioner of Patents and Trademarks*